(12) United States Patent
Saab-Ishmail

(10) Patent No.: US 6,583,280 B1
(45) Date of Patent: Jun. 24, 2003

(54) POLYAMINE ANALOGUES HAVING ANTIPROLIFERATIVE ACTIVITY

(76) Inventor: Nada H. Saab-Ishmail, 6987 Dacosta St., Dearborn Heights, MI (US) 48127

(*) Notice: Subject to any disclaimer, the term of this patent is extended or adjusted under 35 U.S.C. 154(b) by 0 days.

(21) Appl. No.: 09/864,868

(22) Filed: May 25, 2001

Related U.S. Application Data

(60) Provisional application No. 60/207,229, filed on May 26, 2000.

(51) Int. Cl.[7] ..................... A61K 31/395; C07D 245/02
(52) U.S. Cl. ......................................... 540/470; 514/183
(58) Field of Search ........................... 514/183; 540/470

(56) References Cited

PUBLICATIONS

Rolla, Sodium Borohydride Reactions Under Phase–Transfer Conditions: Reduction of Azides to Amines, Journal of Organic Chemistry, vol. 47, No. 22, pp. 4327–4329, 1982.*

Wu et al., Synthesis and Evaluation of a Polyamine Phosphinate and Phosphonamidate as Transition–State Analog Inhibitors of Spermidine/Spermine–N1–Acetyltransferase, Bioorganic & Medicinal Chemistry, vol. 4, No. 6, pp. 825–836, 1996.*

* cited by examiner

*Primary Examiner*—Brenda Coleman
(74) *Attorney, Agent, or Firm*—Glenna Hendricks

(57) ABSTRACT

Novel compounds are chiral compounds which are conformationally restricted polyamine analogues for use in imaging and for therapeutic use in treatment of tumors. These analogues diminish the ability to aggregate DNA seen in the parent polyamines. The invention provides for synthesis of a library of analogues with fine structural modifications which retain restriction and conservation of the molecular weight of the parent polyamines.

3 Claims, No Drawings

POLYAMINE ANALOGUES HAVING ANTIPROLIFERATIVE ACTIVITY

This application takes priority from Provisional Application 60/207,229, filed May 26, 2000.

The work on this invention was supported by a grant from the National Institutes of Health, National Heart, Lung and Blood Institute. Hence, the government of the United States of America has certain rights in this invention.

FIELD OF THE INVENTION

The present invention relates to the field of polyamine analogues having antiproliferative effects.

BACKGROUND OF THE INVENTION

Polyamines (putrescine, spermidine and spermine) are essential for cell growth, proliferation and DNA synthesis. Depletion of cellular polyamines causes cytotoxicity and death. The polyamine biosynthetic pathway and active support system, under normal conditions, are capable of providing the cell with the required quantity of polyamines for appropriate cell growth and reproduction. Polyamine sources include cell turnover, diet and synthesis by GI flora.

According to the polyamine pathway, putrescine is formed from ornithine by the action of the growth related pyridoxal phosphate-dependent ornithine decarboxylase. Putrescine is converted to spermidine and then to spermine through the consecutive action of two distinct aminopropyltransferases, spermidine synthase and spermine synthase. Both of these enzymes use decarboxylated S-adenosyl-L-methionine (dc-AdoMet) as an aminopropyl donor. The dc-AdoMet is a rate limiting substrate which is formed and controlled by the action of pyruvate-S-adenosyl methionine decarboxylase on S-adenosyl-methionine (AdoMet). Polyamines are interconverted and degraded back to putrescine by the action of two enzymes: cytosolic spermidine/spermidine N'acetyltransferase, which acetylate the aminopropyl end using acetyl-CoA and polyamine oxidase to split off 3-acetamidopropionaldehyde.

The high polyamine levels in tumor cells can be attributed to the induced activities of the polyamine biosynthetic enzymes. With respect to this observation, specific and potent inhibitors of each enzyme have been synthesized and evaluated for their antitumor activity. The α-difluoromethylornithine (DFMO, Ki=40 $\mu$M) is an irreversible inhibitor of ODC. DFMO depletes putricine and spermidine pools, but has little effect on Spermine pools, thereby causing a cytostatic rather than a cytotoxic effect. DFMO has also been used as a chemopreventive agent and to potentiate the antitumor effect of cisplatins and carmustine. The U.S. Food and Drug Administration and the World Health Organization have approved DFMO for treatment of African sleeping sickness cause by *T. brudei gambiense*. In clinical trials, the more cytostatic putrescine analogue, (2R, 5R)-6-heptyne-2,5-diamine (RR-MAP, Ki=3 $\mu$m) has been found to cause myclosuppression and renal toxicity. Methylglyoxal-bis-guanylhydrazone (MGBG, Ki<1 $\mu$M), a model compound, is a strong inhibitor of AdoMetDC. Although it is a well-known anticancer drug, MDG suffers from many disadvantages such as lack of specificity for AdoMetDC. The other potent irreversible inhibitor, 5'-{[(Z)-4-anino-2-butenyl]methylamino}-5'-deoxyadenosin (AbeAdo, Ki=0.3 $\mu$M) cures *Trypanosoma brucei brucei*, (at least 100 times more potent than DFMO) and multi-drug-resistant *Trypanosoma brucei rhodesiense* infections in mice. S-(5'-deoxy-5'-adenosyl)-1,8-diamino-3-thiooctane (AdoDATO, IC$_{50}$<50 $\mu$M) and S-(-5'-deoxy-5'-adenosyl)-1,12-diamino-3-thio-9-azadodecane (AdoDATAD, IC$_{50}$=20 $\mu$M) are specific multisubstrate adduct inhibitors (transition state complex analogues) of spermidine synthase and spermine synthase, respectively, mainly used in vitro. Complete and selective depletion of PAO by N'N-bis(2,3-butadienyl)-1,4-butanediamine (MDL 72527, IC$_{50}$=0.04 mg/kg) did not cause any toxic effect. N-[1-(S-coenzyme A)acetyl]-syn-norspermidine amide (CNSA, IC$_{50}$=0.3 $\mu$M) is a potent multisubstrate inhibitor of SSAT devoid of activity in intact cells due to lack of uptake.

The polyamine transport system is stimulated during proliferation and suppressed during differentiation. This transport is an energy dependent, saturable process for polyamines and synthetic analogues traversing intact the plasma membrane. The polyamine transport may also be viewed as a helpful physiological vector to deliver pharmacologically active substances into the cell.

Several polyamine analogues are known. Antiproliferative agents are seen at table I. Some of the N,N'-bis ethylated polyamine analogues are effective antiproliferative agents in L1210 murine leukemia cells. N',N''-bis ethylnorspermine (DENSpm, IC$_{50}$=1.3 $\mu$M), N',N''-bis-ethylspermine (DESpm, IC$_{50}$=0.18 $\mu$M) were able to compete with spermine for uptake, accumulate into the cell and deplete all three polyamine pools. These compounds down-regulate ODC and AdoMet-DC in a manner similar to natural exogenous polyamines and induce SSAT. The norspermine analogues were most effective in reducing the polyamine pools in several cell lines. DENSPM is in phase I clinical trial as an antineoplastic.

SUMMARY OF THE INVENTION

It is the purpose of this invention to develop a new group tetraamines. May of these novel compounds are chiral compounds which are conformationally restricted polyamine analogues for use in imaging and for therapeutic use in treatment of tumors. These analogues diminish the ability to aggregate DNA seen in the parent polyamines. The invention provides for synthesis of a library of analogues with fine structural modifications which retain restriction and conservation of the molecular weight of the parent polyamines.

DETAILED DESCRIPTION OF THE INVENTION

The present invention relates to a new group of tetraamines. It is found that very small structural alterations in polyamine analogues sometimes result in pronounced changes in potency and timing of biological activity. DENSPM has a Ki value for the polyamine transport system of 17 $\mu$M and up-regulates SSAT by 15 fold. DESPM has a faster impact on cell growth at Ki of 1.6 $\mu$M and a 4.6 fold SSAT stimulation. DENSPM also displayed great antiproliferative activity against two human pancreatic ductal adenocarcinoma cell lines. However, there was incomplete depletion of the polyamine pool, suggesting a distinct antiproliferative mechanism.

The effect of polyamine analogues on various cell lines and, hence, the polyamine requirement in each line may be phenotype specific. At 10 $\mu$M concentration, DESpm was shown to be cytotoxic to human large cell carcinoma (LCLC), producing above 1700-fold time- and dose- dependent induction of SSAT. By contrast, although the analogue accumulated to the same extent in the human small cell lung carcinoma line (SCLC), no significant induction of SSAT or cytotoxic effect was observed.

Polyamine analogues that are responsible for SSAT induction also exhibit a characteristic competitive inhibition of the enzyme. These include DENSpm and DESpm. In animal study toxicity, spermidine was approximately one-twentieth as nephro-toxic as spermine.

Polyamine analogues represent a therapeutic approach for the treatment of serious AIDS-related diarrhea (ARD), since they have profound influence on gastric emptying (Table 2). DEHSPM is in phase II clinical trial for treatment of ARD. However, the drug and its metabolites accumulate to toxic levels in the liver and kidney. These problems are not observed with the equal effective hydroxylated compound designate (HO)2DEHPM. The hydroxyl in the R-configuration is a potential 0 site for either conjugation (iI.e., glucuronidation) or further oxidation and clearance. Both analogues have near identical Ki (1.4 and 1.8 $\mu$M), identical 96th $IC_{50}$ (0.05 $\mu$M) toward L1210 cell growth and impact on NMDA receptor (agonist at 0.5-0.1 $\mu$M and antagonist at $\geq$5 $\mu$M). The polyamine pharmacophore can then be manipulated for construction of antitransit, antidiarrheal drugs.

Known polyamines also act as modulators at the N-methyl-D-aspartate (NMDA) receptor. (See table 3.) NMDA function is modulated by several regulatory sites which include a distinct binding site for the polyamines spermine and spermidine. A structure activity relationship between the polyamine analogues and NMDA MK-801 binding properties prove that they all show biphasic agonist/antagonist behavior with homospermine being the most potent agonist (at $\geq$10 $\mu$M, $IC_{50}$=80 $\mu$M). Determination of the length and protonation state of polyamines at physiological pH are important issues. The piperidine norspermine analogue PIP (3,3,3), which is predominantly in the 3+ catonic state (63.2%) is the potent agonist, increasing MK-801 level by 100%. The PYR (3,4,3) is the most potent identified antagonist (pure antagonist, $IC_{50}$=8$\mu$M). The results set the basis for further design of MK-801 agonists and antagonists.

A number of di- and tri-benzyl polyamines were found to be potent selective antagonists at recombinant NMDA over AMPA receptors. Benzylation at either the terminal or central amino groups increases the potency of polyamines. The most potent benzyl derivatives are N4, N9-dibenzylspermine ($,9-DB-3-4-4) and tribenzyl spermidine analogues (TB-3-4, $IC_{50}$=0.2 $\mu$M, TB-3-3) and TB-4-4. Benzyl polyamines represent new tools to study glutamine receptor channels. These compounds may bind sites within the channel that are different from the binding sites for other polyamine derivatives, such as dansyl-polyamines.

Polyamine analogues have been of particular interest to the neuro-oncologist as means of marking brain tumor selectivity. It is suggested that an effective polyamine-based therapy would be enhanced by two approaches: 1) local delivery by intracerebral microdialysis and by 2) polyamine depletion of tumor cells wherein the uptake of tritiated putrescine or tritiated thymidine would be increased. The overload of radioactivity results in lack of growth in inhibited cells.

In another application (Table 4) boron neutron capture therapy (BNCT) has been suggested as a cancer treatment modality. The in vivo biological results in a series of N-(carboranyl-tethered) spermidine, spermine and diethylated analogues show their potential for selectively delivering boron to brain tumor cells, targeting DNA and thereby offering a new class of BNCT agents. All of the synthesized carboranyl polyamines showed toxicity of $IC_{50}$<25$\mu$M, a major limitation in their use. ASPD-5 was the best DNA binder, exhibiting a 28-fold binding affinity enhancement compared to the natural SPD. BBSPD-5 had the lowest in vitro toxicity of all ($IC_{50}$=5000 $\mu$M). The minimal uptake of these compounds limits the usefulness of these compounds as signal delivery agents in BCNT.

It has been postulated that restricted rotation polyamine analogues (Table 5) might bind selectively to DNA, t-RNA or other polyamine binding sites and thereby introduce bends, kinks or loops at their biding domains. Since may of the polyamine receptor sites are chiral in nature, conformationally restrained chiral spermine analogues 2,4-trans (2R, 4S) and 2,4 (2S,4R) have previously been synthesized (Table 5a). A five-member pyrrolidine ring was incorporated into the middle of the spermine molecule, thereby introducing conformational rigidity and chirality at two asymmetric centers. In fact, these analogues are as good a spermine in effecting DNA duples stability at both AT and CG triplexes. This effect can not be solely due to the presence of an additional nitrogen on the pyrrolidine ring. The new spermine analogues are reported as having an extra N right in the middle of the structure of the natural spermine, adding to the considerable flexibility of the terminal aminopropyl fragments.

TABLE 1

Polyamine analogs as Antiproliferative Agents.

| | |
|---|---|
| DENSpm | (structure) |
| CHENSpm | (structure) |
| DESpm | (structure) |
| HSPD | (structure) |

TABLE 2

Antidiarrheals Polyamine Analogue:

(HO)2DEHSpm

DEHSpm

TABLE 3

NMDA receptor and Polyamine Analogue:

PIP(3,3,3)

TB-3-3

PYR(3,4,3)

TB-4-4

TB-3-4

TABLE 3-continued

NMDA receptor and Polyamine Analogue:

4,9-DB-3-4-3

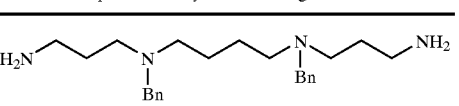

TABLE 4

Polyamine Analogues as BNCT Agents.

ASPD-5

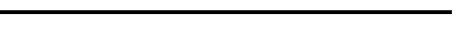

BBSPD-5

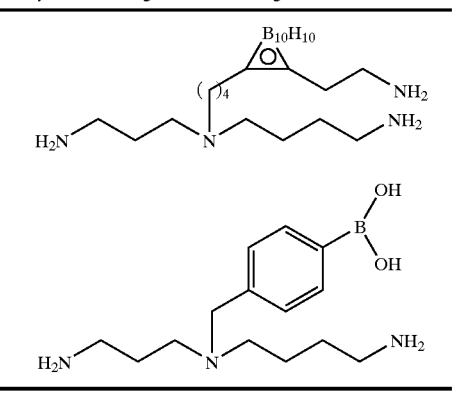

TABLE 5

Restricted Rotation Polyamine Analogues.

a)

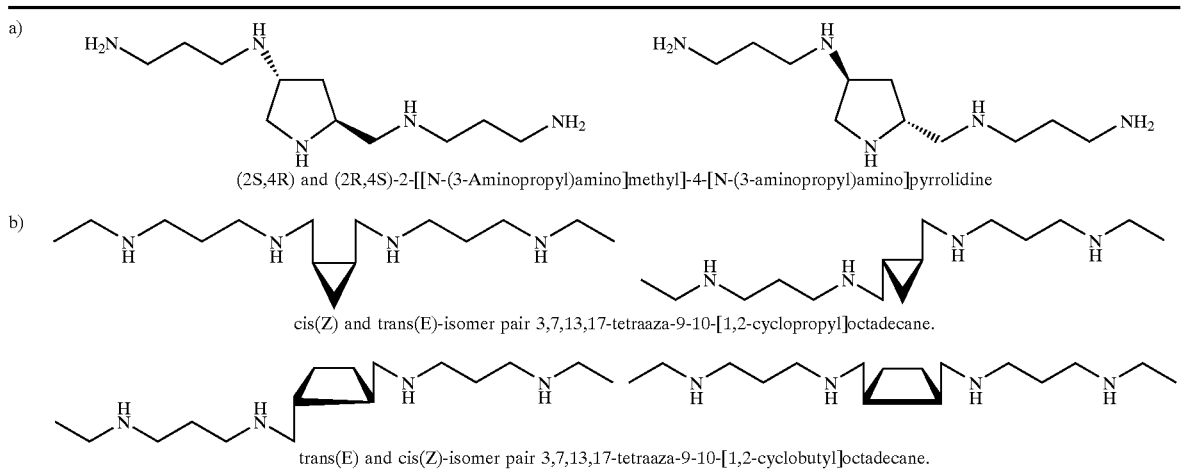

(2S,4R) and (2R,4S)-2-[[N-(3-Aminopropyl)amino]methyl]-4-[N-(3-aminopropyl)amino]pyrrolidine b)

cis(Z) and trans(E)-isomer pair 3,7,13,17-tetraaza-9-10-[1,2-cyclopropyl]octadecane.

trans(E) and cis(Z)-isomer pair 3,7,13,17-tetraaza-9-10-[1,2-cyclobutyl]octadecane.

TABLE 5-continued

Restricted Rotation Polyamine Analogues.

c) 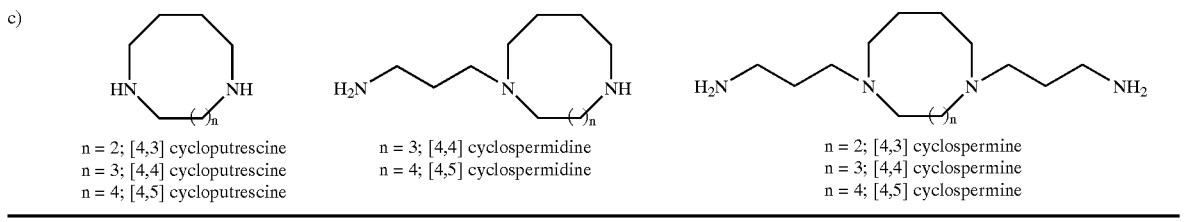

n = 2; [4,3] cycloputrescine
n = 3; [4,4] cycloputrescine
n = 4; [4,5] cycloputrescine n = 3; [4,4] cyclospermidine
n = 4; [4,5] cyclospermidine n = 2; [4,3] cyclospermine
n = 3; [4,4] cyclospermine
n = 4; [4,5] cyclospermine The simple addition of a cyclopropyl or cyclobutyl ring to the butane segment of the DESPM molecule introduces chirality and conformational restriction, These conformationally restricted analogues were found to have good growth inhibitory effects against A459 (lung), HT-29 (colon), U251MG NCI (breast) and DU145 (prostate) human tumor cells. No significant difference in cytotoxicity was observed between the trans- and cis-isomeric pairs.

Other researchers have synthesized a series of spermidine and spermine analogues based on a cycloputrescine (4,n) core and cyclospermidine (4,n) and cyclospermine (4,n) compounds (table 5c). It was found that regidification of spermidine and spermine structures by interconnection of their to secondary amines with a —$(CH_2)_n$— bridge (n=3, 4,5) did not insert a sufficient degree of restriction of these analogues. The amino-propyl fragment still was capable of free rotation. The $CH_2$ bridge resulted in an extra weight added to the structure of the natural polyamines.

The compounds of the invention are of the general formulas:

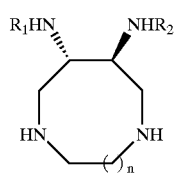

Formula 1 wherein $R_1$ and $R_2$ may each be H or alkyl of 1–6 carbons, and n is 1–3 (n=2 being a norspermine and n=3 being a spermine);

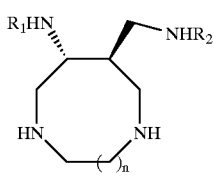

Formula 2 wherein $R_1$ and $R_2$ may be H or alkyl of 1–6 carbons, and n may be 1–3; and

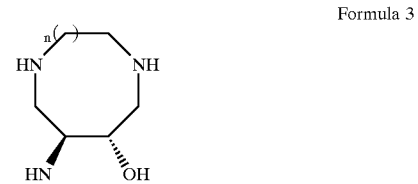

Formula 3 wherein n may be 1–3, with n=2 being norspermidine analogues and n=3 being spermidine analogues; and

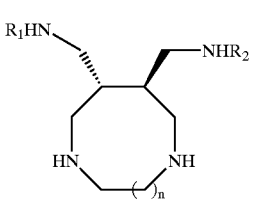

Formula 4 wherein $R_1$ and $R_2$ may be H or alkyl of 1–6 carbons, and n may be 1–3.

The chiral analogues with highly restricted conformation and conservation of molecular weight can bind selectively and efficiently to DNA and diminish the propensity seen in the parent polyamines to aggregate DNA. The molecules may also be derivatized to provide restricted rotation SSAT inhibitors.

The compounds of the invention may be carboxylated to provide suitable compounds for use in imaging. Many compounds used as intermediates prepared during sythesis of the compounds of formulas 1–4 would be useful as imaging agents, including compounds identified as 14–17, 23–28, 30–35, and 42–52. Any or all of the nitrogens in the ring or attached to the ring may be substituted with groups known in the art to introduce imaging properties to amines.

Several schemes are appropriate for preparation of the compounds. For example, N,N'-dibenzyldiamine 11 can be synthesized by the reaction of precursor diamine with benzaldehyde in the presence of $NaBH_4$.

Commercially available 2,3-dibromo-1,4-butanediol in ether was treated with concentrated potassium hydroxide to give chiral (DL) 1,2:3,4-diepoxybutane 12. Dibenzylethyldiamine 11, n=1) was treated with chiral diepoxide 12 to give chiral diaxial-1,2-dihydroxydibenzyl intermediate 13. Mitsunobu procedure was used for the synthesis of dipthtaloyl. The monophthaloyl-monohydroxy intermediate 14 was formed first, isolated and confirmed by NMR and MS.

A second phthaloyl group was also inserted by the same procedure to give the corresponding chiral diequatorial diphthaloyl analogue 15. Intermediate 15 represents a selectively protected polyamine where each of the protecting groups can be separately removed without affecting the other. Deprotection of the phthaloyl group with methanoic hydrazine gave primary diamine 16. Deprotection of the benzylic groups under hydrogen atmosphere using Pd/C as catalyst gave the cyclic polyamine which can be converted to the corresponding tetrachloride salt 1 by treatment with hydrochloric acid and then recrystallized from the appropriate solvents.

Diamine 16 can be protected with 2,4,6-dimethylbenzene-sulfonyl chloride to give the corresponding mesitylenesulfonyl analogue 17. Treatment of 17 with sodium hydride in dimethyl-formamide, followed by dropwise addition of iodoethane, would then produce the diethylated derivative 18. The mesitylene-sulfonyl group can be removed in 30% HBr in acetic acid to give 19. Intermediate 19 can be subjected to hydrogenolysis followed by treatment with HCl to give the corresponding diethylated cyclic tetrahydrochloride polyamine salts.

A)

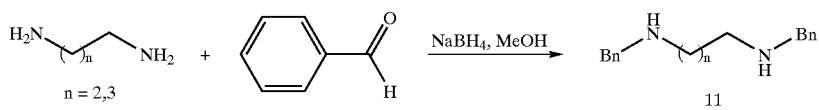

B)

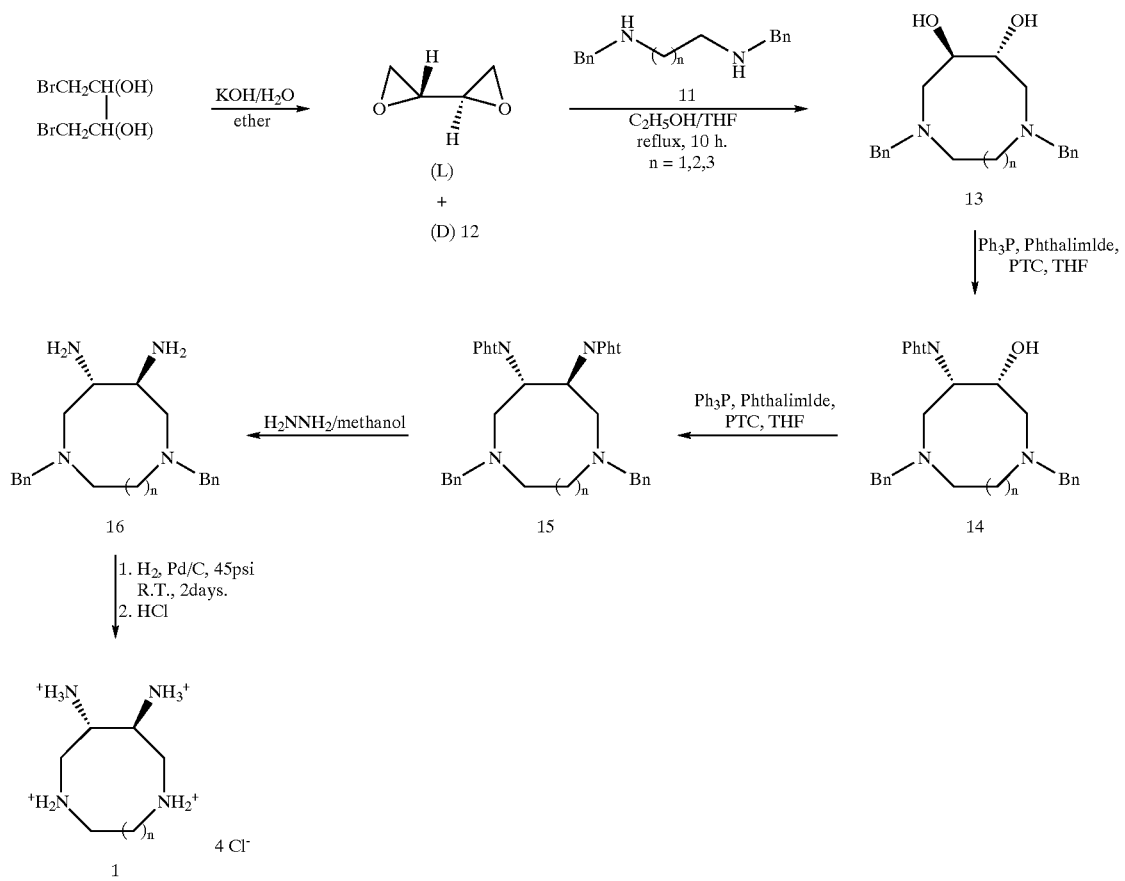

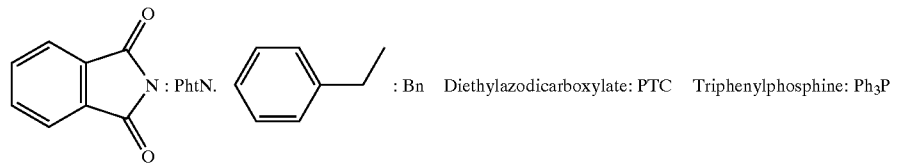

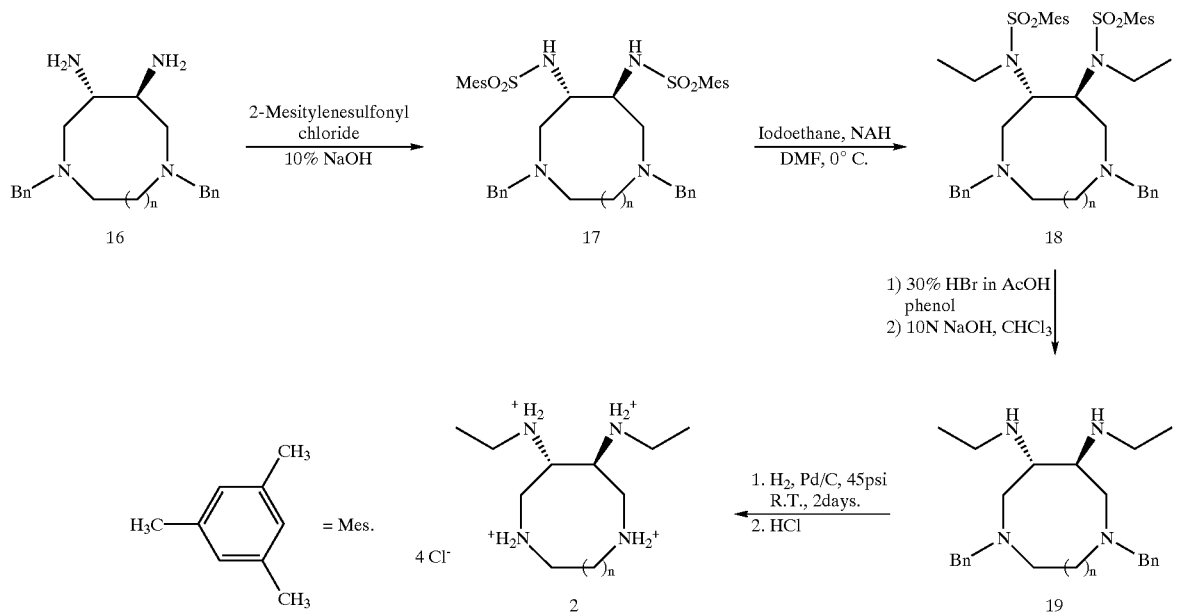

Monoalcohol-monophthaloyl 14 can be converted into the mesylate derivative 20 followed by displacement with azide 21. Azide 21 can be reduced to the corresponding amine 22 using Rolla's procedure (hexadecyltributylphosphonium as a phase transfer catalyst). (See *J. Org. Chem.* 1982, 47, 43270-4329.) Amine 22 can be protected with mesitylenesulfonyl 23 and consequently ethylated 24. Hydrozinolysis of 24 can afford 25. Deprotection of the mesitylenesulfonyl group 26 followed by hydrogenolysis and HCl treatment affords the monoethylated polyamine tetrahydrochloride salts, 3.

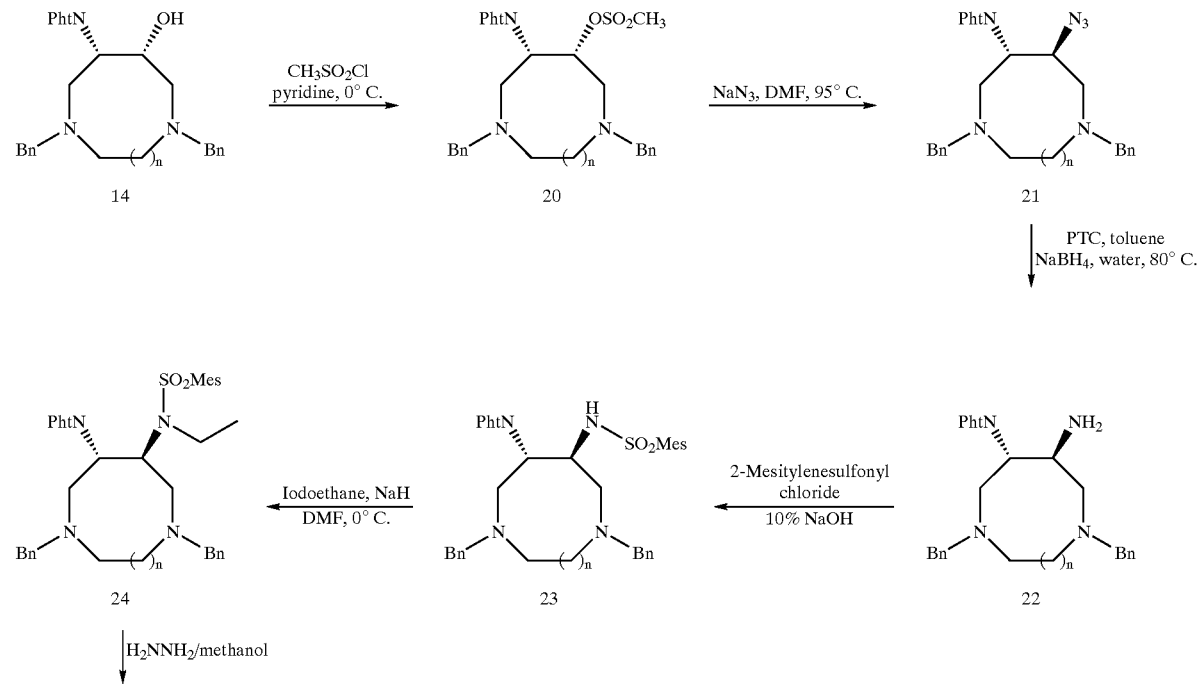

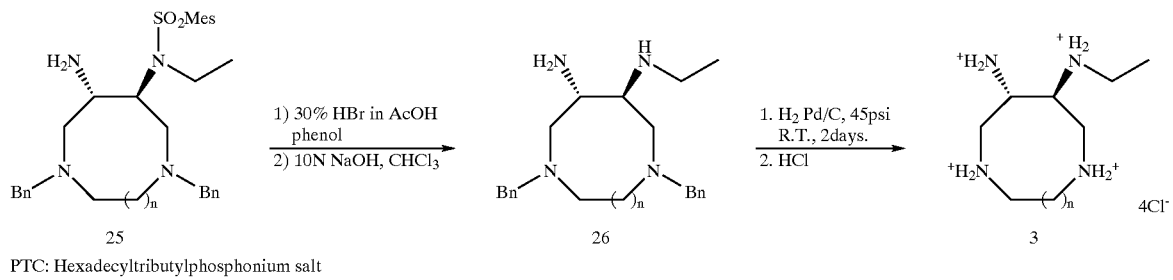

PTC: Hexadecyltributylphosphonium salt

Treatment of intermediate 20 with KCN in the presence of 18-crown-6 gives nitrile 27. The cyano group can be selectively hydrogenated with Raney nickel in methanoic ammonia to give amine 28. Hydrozinolysis of intermediate 28 gives the diamine 29. Consequent hydrogenolysis and HCl treatment gives the tetrahydrochloride polyamine salts, 4.

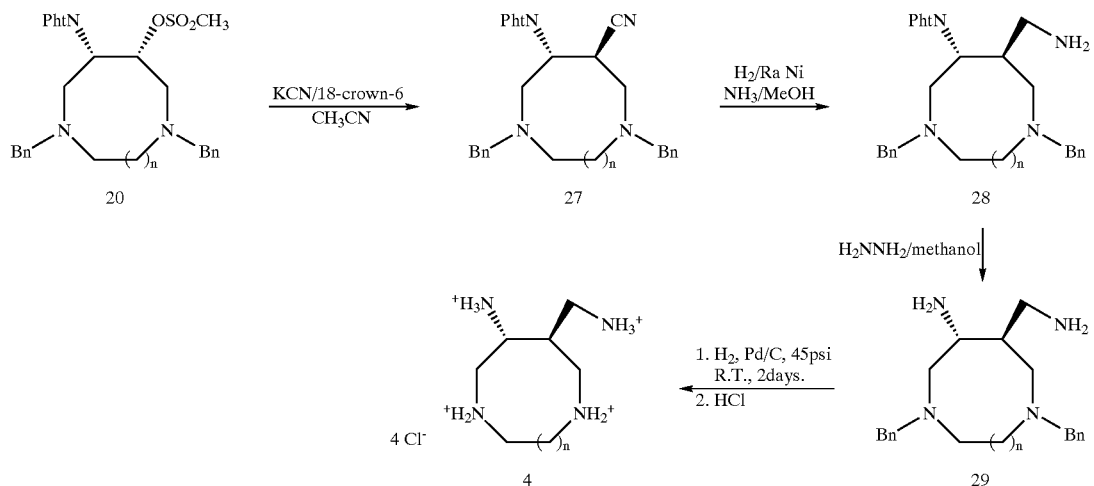

Similarly, diamine 29 can be converted to the corresponding mesityl-protected derivative 30 followed by diethylation to give 31. Removal of the mesitylenesulfonyl group (32) followed by hydrogenolysis and HCl treatment gives the diethylated polyamine tetrahydrochloride salts 5.

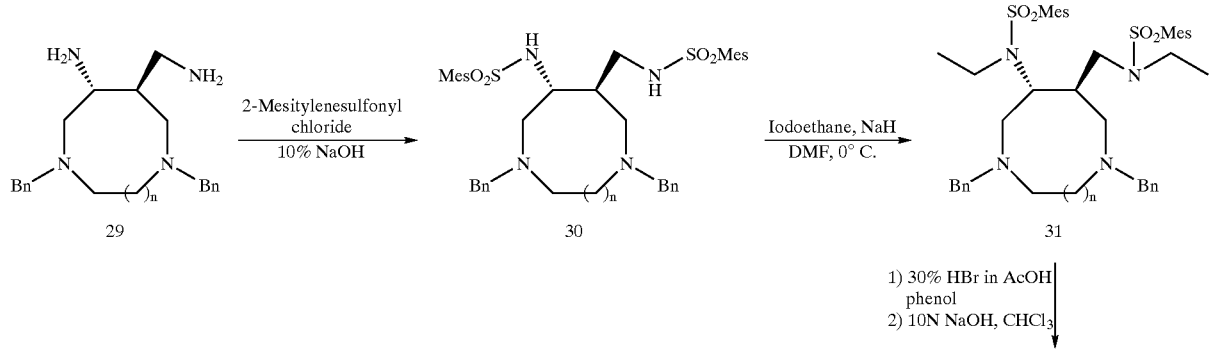

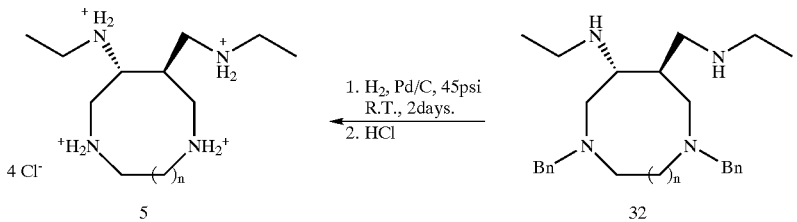

Amine 22 can be converted to the corresponding mesityl-protected analogues 33 which can then be ethylated (34). Hydrozinolysis of 34 can afford 35. Deprotection of mesitylene sulfonyl groups gives 36. Consequently, hydrogenolysis followed by HCl treatment gives the monoethylated tetrahydro-chloride salts, 6.

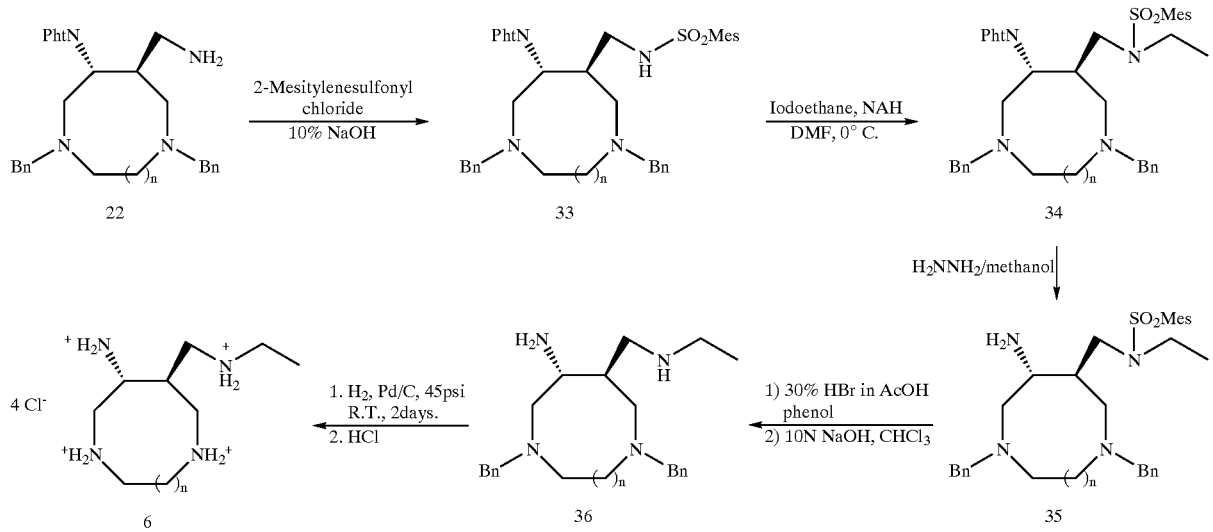

The dihydroxyl intermediate 13 can be protected with trimethylsilylchloride to give 37. Removal of the benzyl group followed by reprotection with di-t-butyoxydicarbonate affords 38. Deprotection of trimethylsilyl groups gives free dialcohol 39, which can be treated with methanesulfonyl chloride to give 40. Treatment of 40 with KCN would give 41, which can be hydrogenated to 42.

Intermediate 42 can be treated with concentrated HCl to give tetrahydrochloride salts, 7. Alternatively, protection of the amino groups with 2-mesitylenesulfonyl chloride gives 43, which can be alkylated with iodoethane to give diethylated 44. Deprotection of both protecting groups can be done using concentrated HCl to give diethylated target compound 8 as hydrochloride salts.

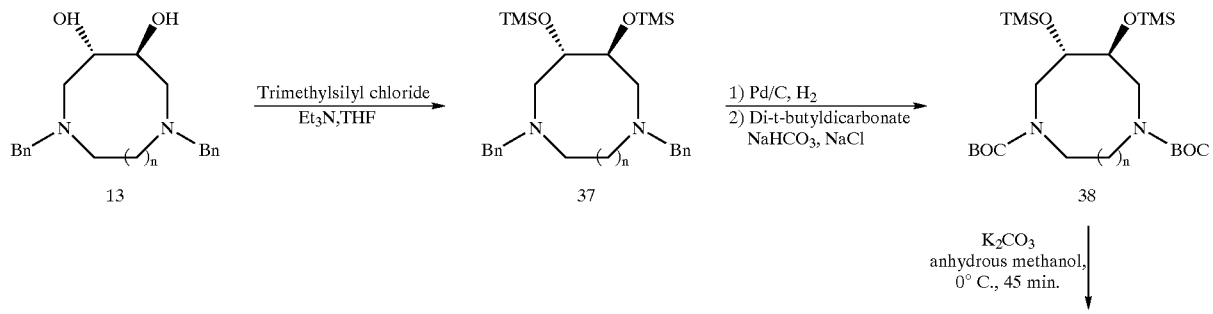

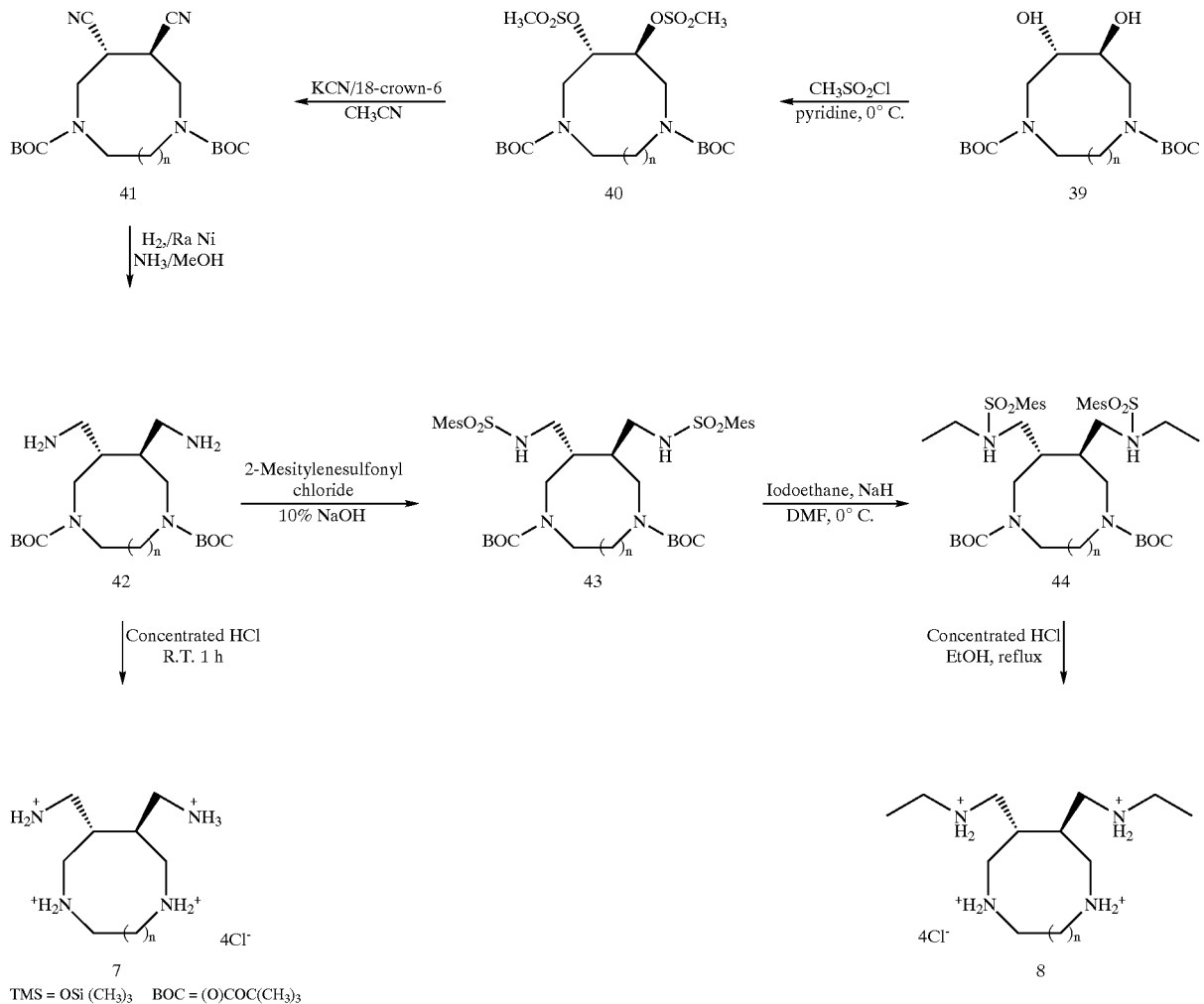

The alcohol 14 was protected with 2-chlorotetrahydrofurane to give 45. Hydrozinolysis gives amine 46, which can be protected with mesitylenesulfonyl (47) and consequently ethylated (48). The alcohol can then be deprotected (49) and converted to the mesylate derivative 50. Treatment of 50 with diethylmethylphosphonite (Arbuzov condtions) can then yield the fully protected phosphinate 51. (See Wu, et al., *Bioorganic and Medicinal Chemistry*, 1996, 4:825-836.) The mesityl and O-ethyl protecting groups can be simultaneously removed (30% HBr) followed by hydrogenolysis to afford the monoethylated phosphinate 9.

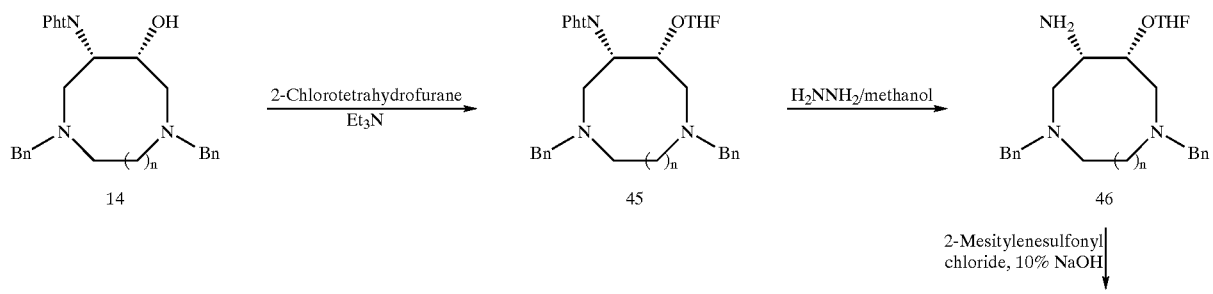

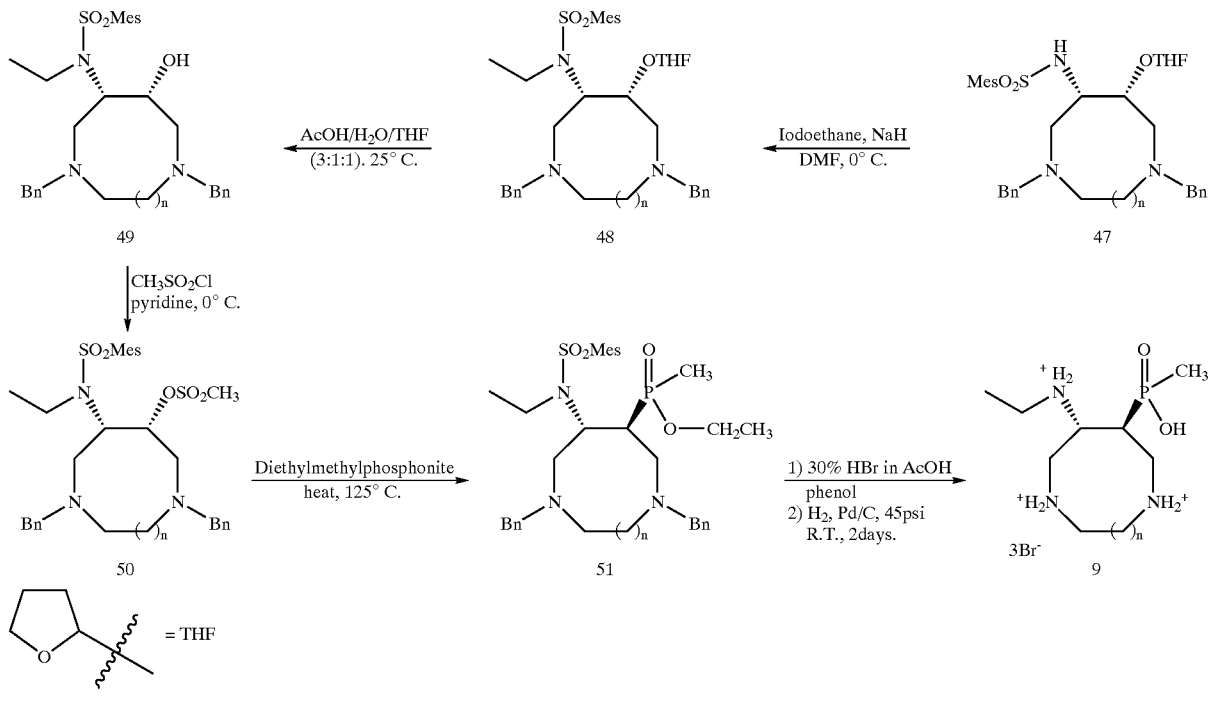

The hydrozinolysis of 14 will afford 52, which then can be converted to hydrochloride salts 10 by hydrogenolysis. The mesitylation of the primary amine in intermediate 35 gives intermediate 53, which can then be alkylated with any convenient alkylation group by usual means. Mesitylation of intermediate 25 can be used to provide compound 54, which can also be alkylated with any convenient alkylation method.

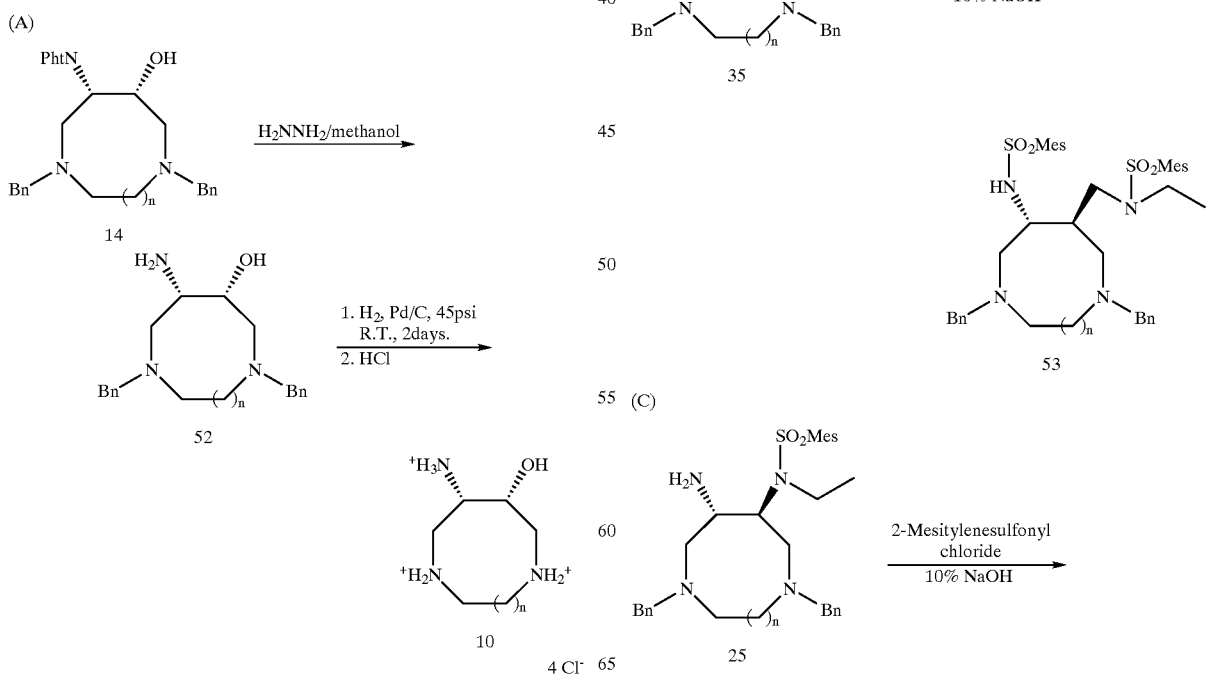

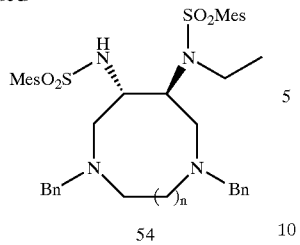

54

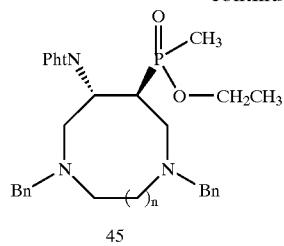

45

1) H₂NNH₂/methanol
2) 30% HBr in AcOH
   phenol
3) H₂, Pd/C, 45psi
   R.T., 2days.

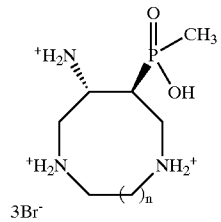

3Br⁻

How a cell "reads" a polyamine analogue is dependent on the molecule's charge and the separation between charges. At physiological pH, many of these tetraamines are expected to exist mainly at the tetracation state, which is important for their activities and incorporation via the polyamine transport apparatus. No bulky substituent is present and an interaction of the protonated terminal nitrogen cation with a biological counterion in the transport apparatus is expected.

Without reliance on any particular mechanism of action, it is postulated that the hydroxyl group in the R-configuration on some analogues may serve as a site for either conjugation or further oxidation and clearance, thereby reducing the toxicity. The metabolically programmed drug would be used in treatment of ARD.

The determination of the length and protonation state of polyamines at physiological pH are also issues that arise in the study of polyamine analogues interaction at NMDA binding sites. The dibenzylated intermediate analogues represent restricted rotation analogues of 4-9-DB-4,4,3, a class of selective NMDA channel blockers. They would be expected to have action compared to bisbenzylated drugs used for treatment of malaria and infections arising from *T. cruzi* and *C. donovan*. The prior art compounds are believed to act by binding to DNA in a manner similar to natural polyamines or to act as bifunctional intercalation agents.

The compounds of the invention can be derivatized to provide specific, targeted contrast and sodium shift agents. The carboxylated compounds, some of which are specifically shown among the intermediates, as previously indicated, represent a class of compounds that are particularly useful for imaging. Both ring nitrogens and nitrogens outside of the ring may be carboxylated to provide imaging agents. The following scheme exemplifies one method of preparation for compounds for use in imaging.

Treatment of the mesylate derivative with diethylmethylphosphonite can yield the fully protected phosphinite 45. This is a selectively protected intermediate wherein each protecting group can be removed without affecting the other groups. The phthaloyl group can be removed by hydrogenolysis and O-ethyl protecting groups can be simultaneously removed using 30% HBr followed by hydrogenolysis to afford the monoethylated phosphinate cyclic polyamine analogues.

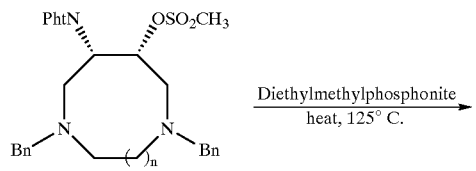

Diethylmethylphosphonite
heat, 125° C.

The pharmacophores of the invention may also be viewed as novel branched macrocycles useful for synthesis of a vast library of contrast agents and sodium shift reagents having desired specificity. Many presently known macrocycles used for synthesis of available contrast agents are too flexible to be useful as highly preorganized agents. In accord with the synthetic pathways disclosed herein, the protecting groups of some intermediates may be selectively removed to allow for selective derivatization of each amine site with the appropriate groups for complexation (such as methyl carboxylate or phosphinic acid groups) to provide selectivity and targeting. Furthermore, the unique characteristics of these molecules makes possible selective deprotection permitting a high degree of control of the number of chelating arms added to the central molecules. Of particular interest is the OH group on compounds of Formula 3, which allows for substitution with particular functionalities to obtain complexation.

The compounds of formulas 1–4 of the invention and substituted analogues may be applied directly to the tumor bed in surgery or may be delivered by shunt to the tumor bed. A concentration of 0.2 to 100 μM in a pharmaceutically acceptable carrier would be appropriate, depending on the identification of the tumor, the weight and age of the patient, would be proposed for such use. Compositions may be administered in the usual pharmaceutically acceptable carriers including saline, buffered saline, glucose in isotonic saline solution, etc. The compositions may be administered in any manner that will cause the active agent to be administered to the tumor. Hence, mode of administration depends on the location of the target tissue.

When administered as a contrast agent, the compositions may be administered in the usual manner, including intravenously.

I claim:

1. A compound which is of the formula:

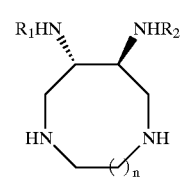

Formula 1 wherein R₁ and R₂ are each chosen from among H and alkyl of 1–6 carbons and n is 1–3.

2. A compound which is of the formula:
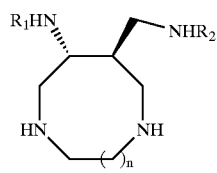
Formula 2
wherein $R_1$ and $R_2$ are each chosen from among H or alkyl of 1–6 carbons and n may be 1–3.
3. A compound of the formula:
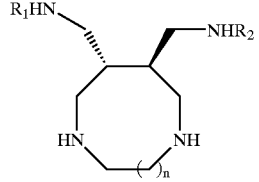
Formula 4
wherein $R_1$ and $R_2$ are each chosen from among H or alkyl of 1–6 carbons and n may be 1–3.
* * * * *